United States Patent [19]

Koyama et al.

[11] Patent Number: 5,146,025
[45] Date of Patent: Sep. 8, 1992

[54] NAPHTHALENE COMPOUNDS

[75] Inventors: Takeshi Koyama, Kanagawa; Takefumi Abe, Niigata, both of Japan

[73] Assignee: Mitsubishi Gas Chemical Company, Inc., Tokyo, Japan

[21] Appl. No.: 478,869

[22] Filed: Feb. 12, 1990

[30] Foreign Application Priority Data

Feb. 28, 1989 [JP] Japan .................................... 1-45430
Feb. 28, 1989 [JP] Japan .................................... 1-45431

[51] Int. Cl.$^5$ ........................ C07C 15/00; C07C 41/00
[52] U.S. Cl. .................... 585/412; 562/467; 568/322; 568/632; 568/747
[58] Field of Search ............... 368/632; 585/412; 568/322, 747

[56] References Cited

U.S. PATENT DOCUMENTS 3,600,445  8/1971  Wirth et al. ................... 260/613
4,386,007  5/1983  Krause .......................... 568/632

FOREIGN PATENT DOCUMENTS 0199636  10/1986  European Pat. Off.
0210929   2/1987  European Pat. Off.

OTHER PUBLICATIONS

Chemical Abstract 53:17065e 1959.

Primary Examiner—Paul J. Killos
Attorney, Agent, or Firm—Browdy and Neimark

[57] ABSTRACT

A compound represented by the formula:

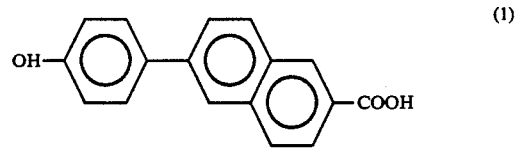

(1)

and a compound represented by the formula:

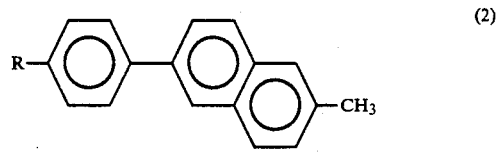

(2)

wherein R is $C_1$-$C_3$ alkyl or $C_1$-$C_3$ alkoxy, which is an intermediate for producing the above compound (1) are disclosed.

12 Claims, 9 Drawing Sheets

NAPHTHALENE COMPOUNDS

BACKGROUND OF THE INVENTION

This invention relates to a naphthalene carboxylic acid which is useful as starting materials for producing a liquid crystal monomer or polymer. This invention also relates to naphthalene compounds for preparing the naphthalene carboxylic acid. Liquid crystal polymers are classified into two types, that is a lyotropic liquid crystal and thermotropic liquid crystal. Recently attention has been drawn to the thermotropic liquid crystal polyester (hereinunder referred to as LCP), because it has excellent flowability and high strength. (Refer to "Plastics", Vol. 3, No. 1, pp. 156–163.) In particular, aromatic LCPs prepared from aromatic carboxylic acids have high strength and good thermal resistance.

In the prior art, aromatic hydroxy carboxylic acids such as p-hydroxy benzoic acid, 2,6-hydroxy naphthoic acid or p-hydroxy biphenyl carboxylic acid and dicarboxylic acids such as terephthalic acid, p-biphenyl dicarboxylic acid or 2,6-naphthalene dicarboxylic acid have been used for synthesizing the aromatic LCPs.

Para-hydroxy benzoic acid and p-hydroxy biphenyl carboxylic acid have been used for preparing liquid crystal monomers. The liquid crystal monomers are used as a starting material for liquid crystal having great dielectric characteristics.

Though the prior aromatic LCPs have high strength and excellent thermal resistance, the melting point of the LCPs is high and the molding properties thereof are poor.

LCPs are used in small and thin-walled electrical and electronic parts. Therefore, development of LCPs having excellent molding properties has been demanded.

SUMMARY OF THE INVENTION

The present inventors have conducted research on starting materials for producing LCPs having excellent molding properties. As a result, we have found 2-(4'-hydroxyphenyl)naphthalene-6-carboxylic acid represented by the formula:

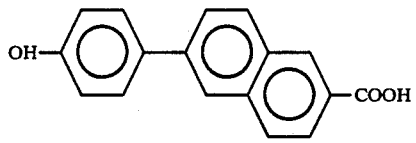

(1)

The compound of formula (1) is prepared from compounds represented by the formula:

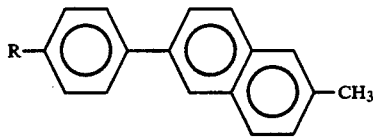

(2)

wherein R is $C_1$–$C_3$ alkyl or $C_1$–$C_3$ alkoxy.

DETAILED EXPLANATION OF THE INVENTION

Figure 1:
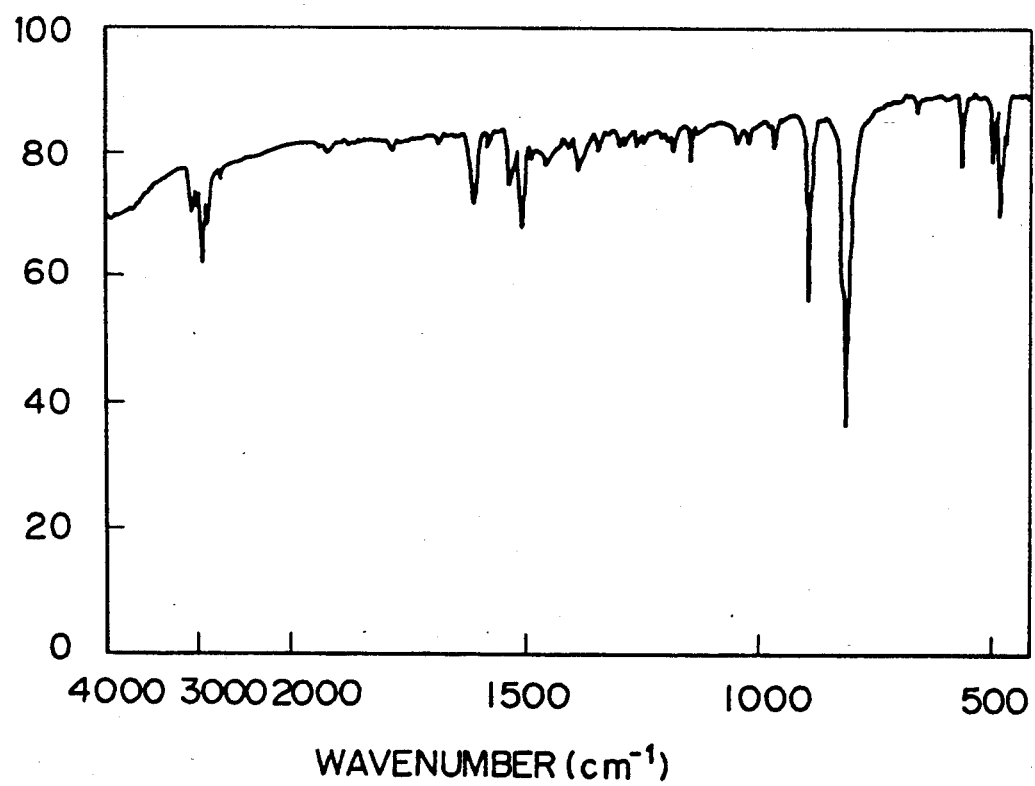
FIG. 1 shows infrared (IR) spectrum of 2-(4'-methylphenyl)-6-methyl naphthalene.

The compounds of formula (2) may be prepared by the following method:

(a) A compound selected from the group consisting of 4-alkoxy biphenyl and 4-alkyl biphenyl is acylated.

The preferable acylation methods are as follows:

(1) The Friedel-Crafts reaction between the above compound and 2-methyl butyric acid chloride and aluminum chloride is carried out to acylate the above compound; or (2) The above compound is reacted with carbon monoxide and 1-butene in the presence of an HF-$BF_3$ catalyst to acylate the above compound. The reaction is as follows:

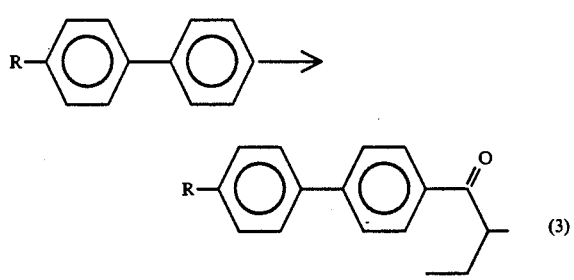

(3)

wherein R is alkyl or alkoxy as defined above.

(b) The acylated compound is reduced to form a hydroxy compound. For example, the acylated compound may be reduced to a hydroxy compound in the absence of hydrogen by using a hydrogen sodium borate catalyst. The acrylated compound may also be reduced to a hydroxy compound in the presence of hydrogen by using a copper chromate catalyst. The reaction is as follows:

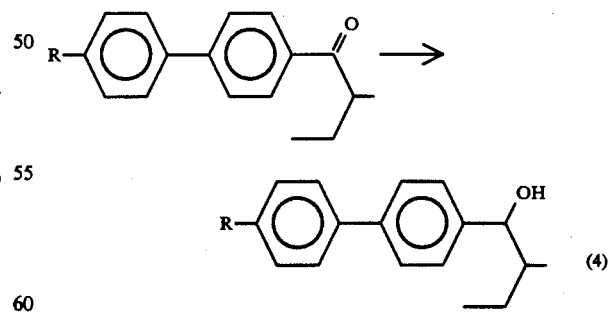

(4)

wherein R is as defined above.

(c) The hydroxy compound is dehydrated in the presence of an acid catalyst to form an olefin compound. Typical examples of the acid catalysts include para-toluene sulfonic acid, hydrochloric acid and dimethyl sulfoxide (liquid phase reaction), and gamma-alumina (vapor phase reaction). The reaction is as follows:

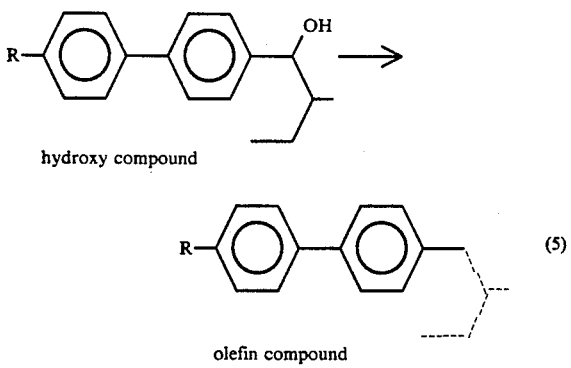

hydroxy compound

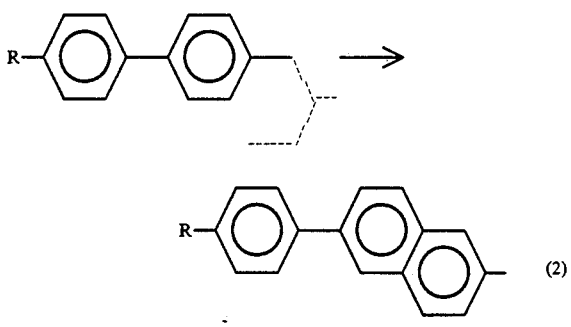

olefin compound wherein R is as defined above and one of the four dotted lines is double bond and others are single bond.

(d) Finally, the vapor phase thermal reaction of the olefin compound is carried out to obtain an object compound in a high yield. Typical examples of the catalysts for the vapor phase thermal reaction include potassium alumina and potassium chromina hold on a carrier. The reaction is as follows:

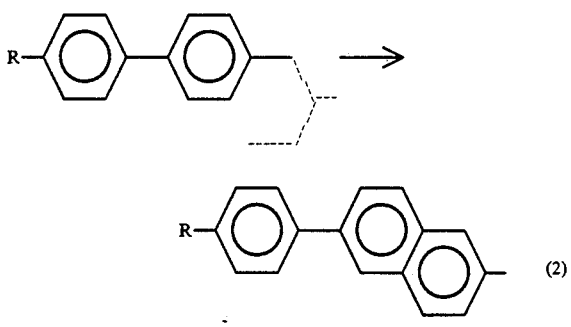

wherein R is as defined above and one of the four dotted lines is double bond and others are single bond.

The compound of formula (1) may be prepared by the following method:

(a) A compound of the formula:

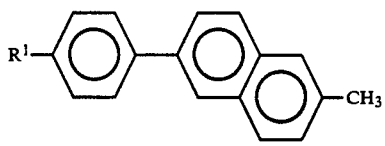

wherein $R^1$ is $C_1$–$C_3$ alkoxy, is oxidized to form a compound represented by the formula:

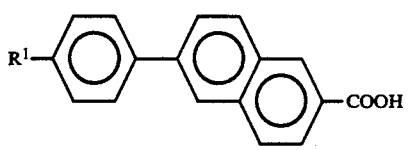

wherein $R^1$ is as defined above. Embodiments of the oxidization are oxidization by potassium permanganate, air oxidization and oxidization by nitric acid.

(b) The compound of formula (7) is hydrolyzed in the presence of an acidic catalyst. A typical example of the catalyst is hydrobromic acid.

When 2-(4'-alkylphenyl)-6-methyl naphthalene is oxidized, 2-phenylnaphthalene-6,4'-dicarboxylic acid is obtained. When 2-(4'-alkoxyphenyl)-6-methyl naphthalene is oxidized and hydrolyzed, 2-(4'-hydroxyphenyl)-naphthalene-6-carboxylic acid is obtained. These compounds are useful as starting materials for liquid crystal polymers and monomers. The naphthalene group is bonded to the phenyl group in the liquid crystal polymers derived from the above compounds, so that the rigidity of the resulting liquid crystal polymers is relaxed which results in lower melting temperature thereof. Therefore, the resulting liquid crystal polymers have excellent molding properties and thermal resistance.

This invention is further explained by way of the following non-limiting examples. All percentages are on a weight basis, unless specified otherwise.

EXAMPLE 1

(Acylation of Alkyl Biphenyl)

Into a 500 ml four-necked flask equipped with a stirring rod, dropping funnel, reflux condenser and thermometer were charged 24.0 g (0.18 mol) of aluminum chloride and 50 ml of methylene chloride. The mixture was stirred and the flask was cooled in an ice-water bath, and 21 g (0.17 mol) of 2-methyl butyryl chloride was dropwise added to the mixture from one dropping funnel. A solution of 25 g (0.15 mol) of p-methyl biphenyl in 50 ml of methylene chloride was dropwise added to the mixture from another dropping funnel, so that the temperature of the mixture did not exceed 10° C. After the addition was completed, the mixture was stirred for 1 hour, and then the mixture was heated under refluxing for a further hour.

After the reaction was completed, the mixture was cooled in an ice-water bath. Water is gradually dropwise added to the reaction mixture to hydrolyze the aluminum chloride.

Toluene (100 ml) was added to the reaction mixture and then the reaction mixture was neutralized. The object product was extracted with the toluene. The toluene solution was dried with sodium sulfate to remove the toluene. Twenty-two grams of 4-methyl-4'-(2-methyl)butyryl biphenyl was obtained by vacuum-distillation (176° C., 1 mmHg). The yield of the product was 59 mol % on the basis of p-methyl biphenyl used.

The analysis data of nuclear magnetic resonance (NMR) and infrared absorption (IR) of the product were as follows:

NMR (CCl$_4$) δ (ppm): 0.90 (CH$_3$, t, J=6.5 Hz), 1.17 (CH$_3$, d, J=6.5 Hz), 1.65 (CH$_2$, q of d, J=6.5 Hz), 3.35 (CH, t of q, J=6.5 Hz), 2.40 (CH$_3$, s), 7.18, 7.45 (=CH, AB type, J=8 Hz), 7.57, 7.95 (=CH, AB type, J=8 Hz)

IR (KBr) cm$^{-1}$: 1680 (conjugated ketone, s)

EXAMPLE 2

(Acylation of Methoxybiphenyl)

Into a 500 ml four-necked flask equipped with stirring rod, dropping funnel, reflux condenser and thermometer were charged 19.0 g (0.14 mol) of aluminum chloride and 100 ml of carbon disulfide. The mixture was stirred. The flask was cooled in an ice-water bath and then 15.3 g (0.13 mol) of 2-methyl butyryl chloride was gradually dropwise added to the mixture from one dropping funnel. A solution of 23 g (0.13 mol) of p-methoxy biphenyl in 50 ml of carbon disulfide was dropwise added to the mixture from another dropping funnel, so that the temperature of the mixture did not exceed 10° C. After the addition was completed, the mixture was stirred for 1 hour and then the mixture was heated under reflux for a further hour.

After the reaction was completed, the reaction mixture was cooled in an ice-water bath, and water was gradually dropwise added to the reaction mixture to hydrolyze the aluminum chloride. After the reaction mixture was neutralized, the object product was extracted with the carbon disulfide. The carbon disulfide solution was dried with sodium sulfate to remove the carbon disulfide. The white solid material was obtained, and then the material was recrystallized with toluene. Twenty grams of 4-methoxy-4'-(2-methyl)butyryl biphenyl was obtained. The yield of the product was 60 mol % on the basis of the p-methoxybiphenyl used.

The analysis data of NMR and IR of the product were as follows:

NMR (CCl$_4$) $\delta$ (ppm): 0.93 (CH$_3$, t, J=6 Hz), 1.18 (CH$_3$, d, J=6 Hz), 1.67 (CH$_2$, q of d, J=6 Hz), 3.35 (CH, t of q, J=6 Hz), 3.83 (CH$_3$O, s), 6.88, 7.45 (=CH, AB type, J=9 Hz), 7.53, 7.93 (=CH, AB type, J=8 Hz)

IR (KBr) cm$^{-1}$: 1675 (conjugated ketone, s), 1035 (CH$_3$O, m)

EXAMPLE 3

(Synthesis of Alkyl Hydroxy Compound)

Into a 300 ml four-necked flask equipped with stirring rod, dropping funnel, reflux condenser and thermometer were charged 2.0 g (0.053 mol) of hydrogen sodium borate, 0.5 g (0.013 mol) of sodium hydroxide and 23.0 g of isopropyl alcohol. The mixture was stirred and solution of 21.8 g (0.086 mol) of 4-methyl-4'-(2-methyl)-butyryl biphenyl of Example 1 in 20 g of isopropyl alcohol was gradually dropwise added to the mixture from a dropping funnel. After the addition was completed, the mixture was heated for 3 hours under reflux with stirring.

After the reaction was completed, the flask was cooled in an ice-water bath. Water was gradually dropwise added to the mixture to hydrolyze the aluminum chloride. Toluene (100 ml) was added to the reaction mixture and the reaction solution was neutralized. The object product was extracted with the toluene. The toluene solution was dried with sodium sulfate to remove the toluene. Twenty-one grams of crude 4-methyl-4'-(1-hydroxy-2-methyl)butyryl biphenyl was obtained. The yield of the product was 96 mol % on the basis of 4-methyl-4'-(2-methyl)butyryl biphenyl used.

The analysis data of NMR and IR of 4-methyl-4'-(1-hydroxy-2-methyl)butyryl biphenyl were as follows:

NMR (CCl$_4$) $\delta$ (ppm): 1.03 (CH$_3$, t, J=8 Hz), 1.05 (CH$_3$, d, J=8 Hz), 1-2 (CH$_2$ and CH, multiplet), 2.40 (CH$_3$, s), 7.30, 7.63 (=CH, AB type, J=8 Hz), 7.50 (=CH, broad s)

IR (KBr) cm$^{-1}$: 3400 (OH, m)

EXAMPLE 4

(Synthesis of Methoxy Hydroxy Compound)

Into a 300 ml four-necked flask equipped with stirring rod, dropping funnel, reflux condenser and thermometer were charged 2.0 g (0.053 mol) of hydrogen sodium borate, 0.5 g (0.013 mol) of sodium hydroxide and 23.0 g of isopropyl alcohol. The mixture was stirred. A solution of 21.8 g (0.086 mol) of 4-methoxy-4'-(2-methyl)butyryl biphenyl of Example 2, 20 g of isopropyl alcohol and 20 g of tetrahydrofuran was gradually dropwise added to the mixture. After the addition was completed, the mixture was heated under reflux with stirring for 3 hours.

After the reaction was completed, the flask was cooled in an ice-water bath. Water was gradually dropwise added to the mixture to hydrolyze the aluminum chloride. Toluene (100 ml) was added to the reaction mixture and the reaction was neutralized. The object product was extracted with the toluene. The toluene solution was dried with sodium sulfate to remove the toluene. Twenty-three grams of crude-4-methoxy-4'-(1-hydroxy-2-methyl)butyryl biphenyl was obtained. The yield of the product was 99 mol % on the basis of 4-methoxy-4'-(2-methyl)butyryl biphenyl used.

The analysis data of NMR and IR of 4-methoxy-4'-(1-hydroxy-2-methyl)butyryl biphenyl were as follows:

NMR (CCl$_4$) $\delta$ (ppm): 0.85 (CH$_3$, t, J=8 Hz), 0.90 (CH$_3$, d, J=8 Hz), 1-2 (CH$_2$ and CH, multiplet), 3.82 (CH$_3$O, s), 6.85, 7.40 (=CH, AB type, J=8 Hz), 7.36 (=CH, broad s)

IR (KBr) cm$^{-1}$: 3400 (OH, m), 1035 (CH$_3$O, m)

EXAMPLE 5

(Synthesis of Alkyl Olefin Compound)

Into a 300 ml four-necked flask equipped with stirring rod, reflux condenser with oil-water separator and thermometer were charged 1.0 g of para-toluene sulfonic acid, 33 g (0.13 mol) of 4-methyl-4'-(1-hydroxy-2-methyl)butyryl biphenyl of Example 3 and 200 ml of benzene. The mixture was stirred. The mixture was heated under reflux with stirring to distill the azeotropic mixture of benzene and water formed by the dehydrogenation reaction. The azeotropic mixture was liquefied in the reflux condenser. Only water was removed by the oil-water separator. The reaction was completed in 3 hours.

After the reaction mixture was neutralized, the object product was extracted with benzene. The benzene solution was dried with sodium sulfate to remove the benzene. Gas liquid chromatograph analysis (GLC) shows that the residue is 4-methyl-4'-isopentenyl biphenyl (olefin compound), and that the olefin compound contains four kinds of isomers in which the positions of double bond are different from each other. Olefin compound (29.6 g) was obtained. The yield of the product was 96 mol % of the basis of 4-methyl-4'-(1-hydroxy-2-methyl)butyryl biphenyl used.

The analysis data of NMR and IR of the olefin compound were as follows:

NMR (CCl$_4$) (peak of main product) $\delta$ (ppm): 1.33 (CH$_3$, t, J=7 Hz), 1.98 (CH$_3$, d, J=7 Hz), 2.33 (CH$_2$, q, J=7 Hz), 2.40 (CH$_3$, s), 6.38 (=CH, broad s), 7.30, 7.63 (=CH, AB type, J=8 Hz), 7.61, 7.32 (=CH, AB type, J=8 Hz)

IR (KBr) cm$^{-1}$: 1610 (C=C, m)

EXAMPLE 6

(Synthesis of Alkoxy Olefin Compound)

Into a 300 ml four-necked flask equipped with stirring rod, reflux condenser with oil-water separator and thermometer were charged 1.0 go of para-toluene sulfonic acid, 16.4 g (0.061 mol) of 4-methoxy-4'-(1-hydroxy-2-methyl)butyryl biphenyl of Example 4 and 200 ml of benzene. The mixture was stirred. The mixture was stirred and heated under reflux with stirring to distill the azeotropic mixture of benzene and water formed by the dehydrogenation reactor. The azeotropic mixture was liquefied in the reflux condenser. Only water was removed by the oil-water separator. The reaction was completed in 3 hours.

After the reaction mixture was neutralized, the object product was extracted with benzene. The benzene solution was dried with sodium sulfate to remove the benzene. Gas liquid chromatograph analysis (GLC) shows that the residue is 4-methoxy-4'-isopentenyl biphenyl (olefin compound), and that the olefin compound contains four kinds of isomers in which the double bond positions are different from each other. Olefin compound (13.5 g) was obtained. The yield of the product was 88 mol % of the basis of 4-methoxy-4'-(1-hydroxy-2-methyl)butyryl biphenyl used.

The analysis data of NMR and IR of the olefin compound were as follows:

NMR (CCl$_4$) (peak of main product) δ (ppm): 1.15 (CH$_3$, t, J=7 Hz), 1.88 (CH$_3$, d, J=7 Hz), 2.22 (CH$_2$, q, J=7 Hz), 3.82 (CH$_3$O, s), 6.25 (=CH, broad s), 6.85, 7.45 (=CH, AB type, J=8 Hz), 7.15, 7.43 (=CH, AB type, J=8 Hz)

IR (KBr) cm$^{-1}$: 1610 (C=C, m), 1040 (CH$_3$O, s)

EXAMPLE 7

[Synthesis of 2-(4'-Alkylphenyl)-6-Methyl Naphthalene]

Into a reactor having an internal diameter of 30 mm and a length of 300 mm was charged 50 g of chromia-alumina-5% potassium carrier catalyst (Nissan Gardlar, G41PC). A nitrogen gas was flowed through the reactor at a rate of 50 l/hour. The reactor was heated to 500° C.

Into the reactor were fed a solution of 12.4 g (0.56 mol) of the four isomers of 4-methyl-4'-isopentenyl biphenyl of Example 5 in 237.6 g of toluene at a rate of 10 g/hour. Lower boiling point compounds were removed by distillation from the reaction mixture. The reaction mixture was concentrated to 30 g. The reaction mixture was left to stand. The deposited crystal was filtered to separate it off. The product was recrystallized with toluene for purification. As a result, 2-(4'-methylphenyl)-6-methyl naphthalene (5.0 g) was obtained. The yield of the product was 39 mol % on the basis of the olefin compound (4-methyl-4'-isopentenyl biphenyl).

Figure 2:
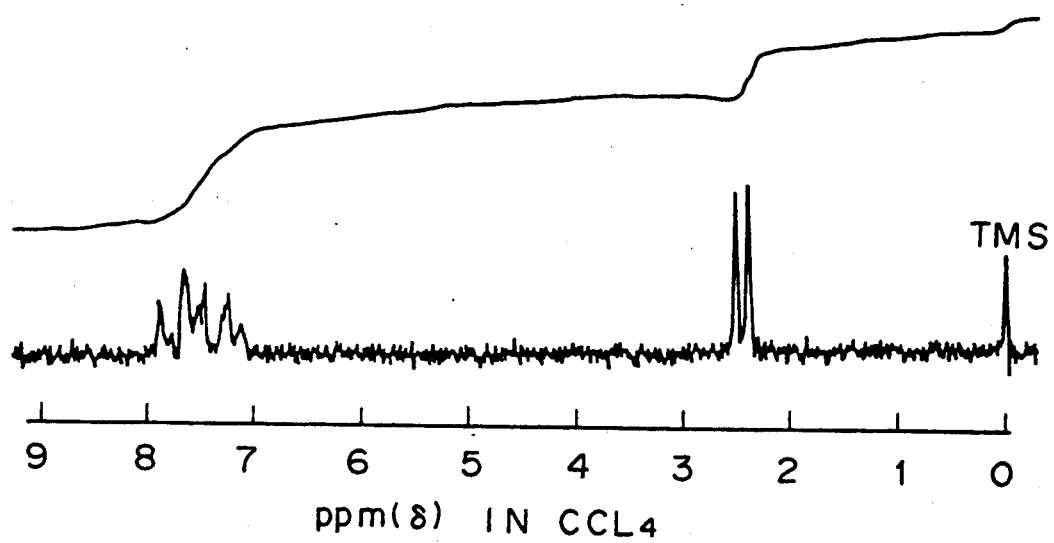
FIG. 2 shows the nuclear magnetic resonance (NMR) spectrum of 2-(4'-methylphenyl)-6-methyl naphthalene.
Figure 3:
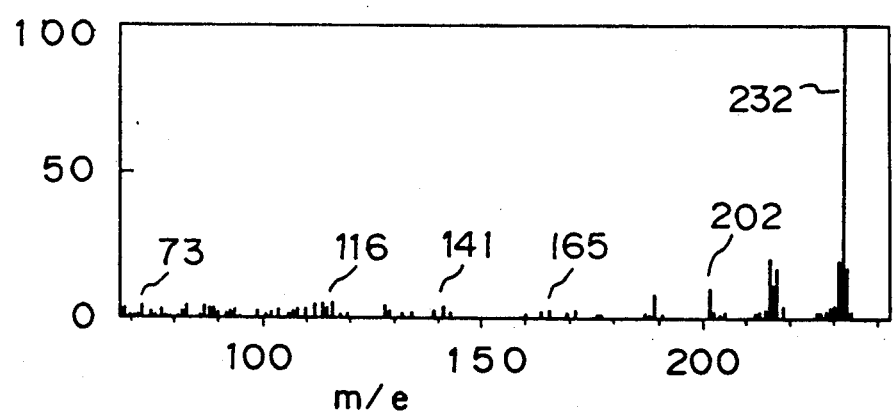
FIG. 3 shows the mass spectrum of 2-(4'-methylphenyl)-6-methyl naphthalene.

IR spectrum, NMR spectrum and mass spectrum (MS) of the product are shown in FIGS. 1-3, respectively.

The element analysis was as follows:
Theoretical (C$_{18}$H$_{16}$): C 93.06%, H 6.94%
Found: C 92.44%, H 6.85%

The analysis data of NMR, IR and MS of the product were as follows:

NMR (CCl$_4$) δ (ppm): 2.52 (CH$_3$, s), 2.40 (CH$_3$, s), 7.88 (=CH, broad s), 7.18, 7.53 (=CH, AB type, J=7 Hz), 7.58, 7.78 (=CH, d, J=6 Hz)

IR (KBr) cm$^{-1}$: 3010 (w), 2910 (m), 1600 (m), 1500 (m), 890 (m), 820 (s)

MS m/s M+232 (base peak)
melting point: 126°-127° C.

EXAMPLE 8

[Synthesis of 2-(4'-Alkoxyphenyl)-6-Methyl Naphthalene]

Into a reactor having an internal diameter of 30 mm and a length of 300 mm was charged 50 g of chromia-alumina-5% potassium carrier catalyst (Nissan Gardlar, G41PC). A nitrogen gas was flowed through the reactor at a rate of 50 l/hour. The reactor was heated to 500° C.

Into the reactor were fed a solution of 12.4 g (0.049 mol) of the four isomers of 4-methoxy-4'-isopentenyl biphenyl of Example 6 in 237.6 g of toluene at a rate of 10 g/hour. Lower boiling point compounds were removed by distillation from the reaction mixture. The reaction mixture was concentrated to 30 g. The reaction mixture was left to stand. The deposited crystal was filtered to separate it off. The product was recrystallized with toluene for purification. As a result, 2-(4'-methoxyphenyl)-6-methyl naphthalene (5.0 g) was obtained. The yield of the product was 45 mol % on the basis of the olefin compound (4-methoxy-4'-isopentenyl biphenyl).

Figure 4:
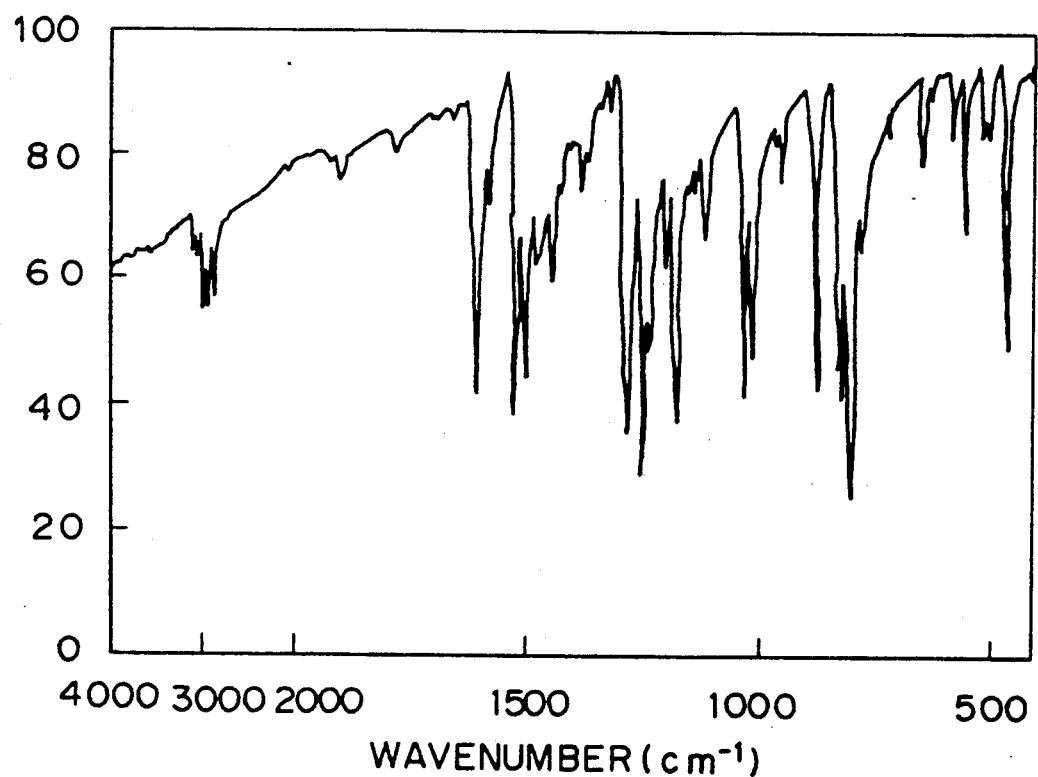
FIGS. 4–6 show the IR spectrum, NMR spectrum and mass spectrum of 2-(4'-methoxyphenyl)-6-methyl naphthalene, respectively.
Figure 5:
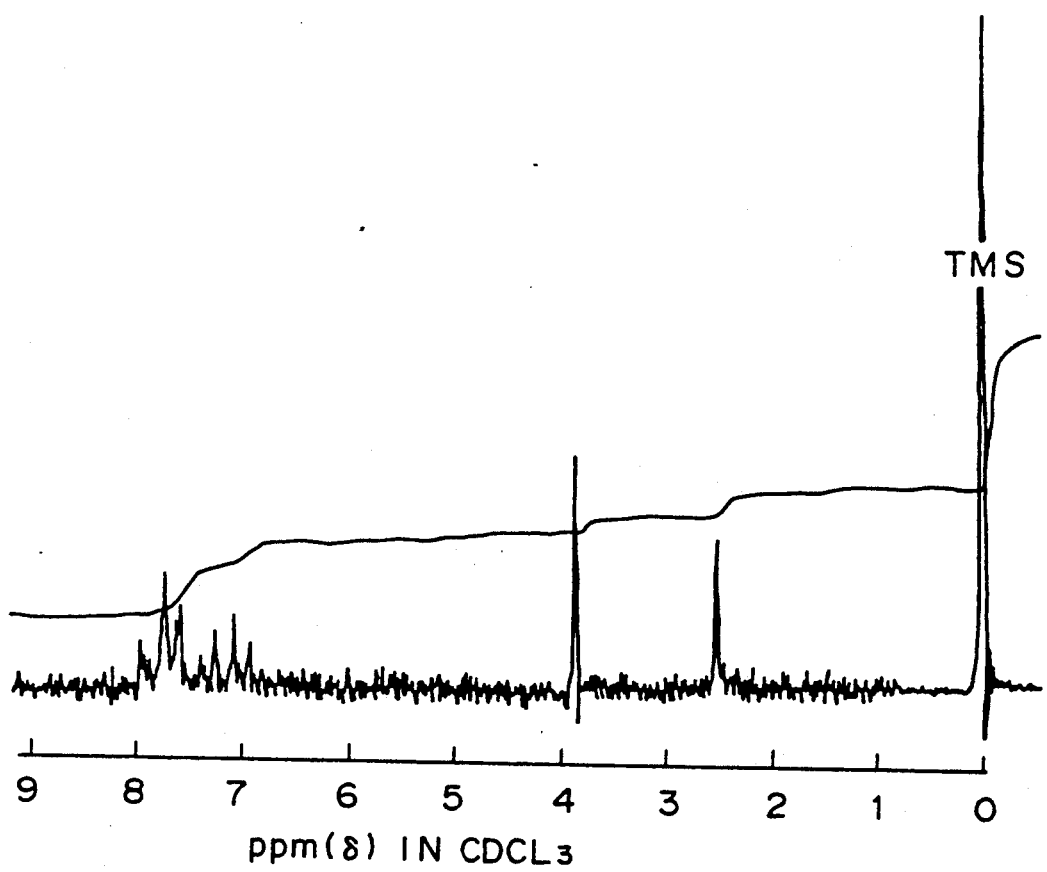
Figure 6:
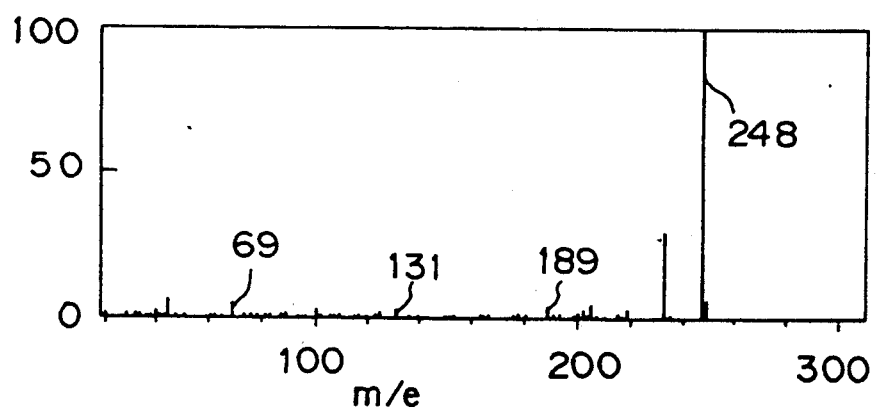

IR spectrum, NMR spectrum and mass spectrum (MS) of the product are shown in FIGS. 4-6, respectively.

The element analysis was as follows:
Theoretical (C$_{18}$H$_{16}$O): C 87.06%, H 6.49% Found: C 86.46%, H 6.33%

The analysis data of NMR, IR and MS of the product were as follows:

NMR (CDcl$_3$) δ (ppm): 2.53 (CH$_3$, s), 3.88 (CH$_3$O, s), 7.70 (=CH, broad s), 7.00, 7.30 (=CH, AB type, J=8 Hz), 7.90, 7.63 (=CH, d, J=7 Hz)

IR (KBr) cm$^{-1}$: 3050 (w), 3010 (w), 2960 (w), 2910 (w), 1605 (s), 1520 (s), 1040 (s), 1020 (s), 820 (s)

MS m/s M+248 (base peak)
melting point: 315°-316° C.

EXAMPLE 9

(Synthesis of 2-(4'-Methoxyphenyl)Naphthalene-6-Carboxylic Acid)

Into a four-necked flask equipped with a stirring rod, dropping funnel, reflux condenser and thermometer were charged 2.0 g (0.0081 mol) of 2-(4'-methoxyphenyl)-6-methyl naphthalene of Example 8, 80 ml of pyridine and 40 ml of water. The mixture was heated to 96°-97° C. under reflux with stirring.

About 0.25 g of potassium permanganate was added to the mixture 24 times at an interval of about 7 minutes. The total amount of potassium permanganate added was 5.1 g (0.032 mol), and the total time over which potassium permanganate was added was about 4 hours. After the addition was completed, the mixture was heated for a further hour. After the reaction was completed, the black precipitate (manganese dioxide) was removed by filtration to obtain filtrate (A). The precipitate was added to 50 ml of pyridine, and the mixture was heated with stirring. The mixture was filtered to obtain filtrate (B). Precipitates (A) and (B) were combined. Half of the solvent in the combined filtrate was removed by distillation. Two hundred milliliters of toluene was added to the residue, and unreacted components were extracted and recovered with the toluene. The toluene was removed from the extract. As a result, 1.4 g of 2-(4'-methoxyphenyl)-6-methyl naphthalene which is the starting material was recovered. The reactivity was 30%.

After the unreacted component was recovered, the solvent was removed from the reaction mixture by distillation to obtain 0.72 g of 2-(4'-methoxyphenyl)-naphthalene-6-carboxylic acid. The yield of the product was 99 mol % on the basis of 2-(4'-methoxyphenyl)-6-methyl naphthalene used. The purity of the product was 98%. The analysis data of elemental analysis, NMR, IR and MS of the resulting 2-(4'-methoxyphenyl)-6-carboxylic acid are as follows:

Elemental analysis:
theoretical ($C_{18}H_{14}O_3$): C 77.70%, H 5.04% found: C 77.67%, H 5.14%

NMR [$(CD_3)_2SO$] δ (ppm): 3.83 (CH, s), 7.09, 7.80 (CH=AB type, J=8.8 Hz), 8.00, 8.17 (=CH, d, J=8.8 Hz), 8.03 (=CH, s), 8.61 (OH, s)

IR (KBr) ν ($cm^{-1}$): 3000-2500 (COOH, broad), 1690 (CO, s), 1040 ($OCH_3$, m)

MS m/e M+278 (base peak)

EXAMPLE 10

[Synthesis of 2-(4'-Hydroxyphenyl)Naphthalene-6-Carboxylic Acid]

Into a four-necked flask equipped with a stirring rod, dropping funnel, reflux condenser and thermometer was charged 0.63 g (0.0023 mol) of 2-(4'-methoxyphenyl)naphthalene-6-carboxylic acid of Example 9. To the compound were added 50 ml of acetic acid, 30 ml of acetic anhydride and 15 ml of 48% hydrobromic acid. The reaction was continued for 10 hours while the mixture was being heated with stirring, thereby obtaining clear solution. When 50 ml of water was added to the reaction solution, white precipitate was obtained. The precipitate was separated from the mixture by filtration, and then dried to obtain 0.5 g of 2-(4'-hydroxyphenyl)naphthalene-6-carboxylic acid. The yield of the product was 82 mol % on the basis of 2-(4'-methoxyphenyl)naphthalene-6-carboxylic acid used. The purity of the produce was 98%.

The analysis data of elemental analysis, NMR, IR and MS of 2-(4'-hydroxyphenyl)naphthalene-6-carboxylic acid.

Elemental Analysis:
theoretical ($C_{18}H_{12}O_3$): C 77.27%, H 4.58% found: C 76.77%, H 4.75%

NMR [$(CD_3)_2SO$] δ (ppm): 6.88, 7.65 (CH=AB type, J=8.6 Hz), 7.85, 8.10 (=CH, d, J=8.8 Hz), 7.97 (=CH, s), 8.56 (COOH, s), 9.60 (OH, s)

IR (KBr) ν ($cm^{-1}$): 3000-2500 (COOH, broad), 1680 (CO, s)

MS m/e M+264 (base peak)

Figure 7:
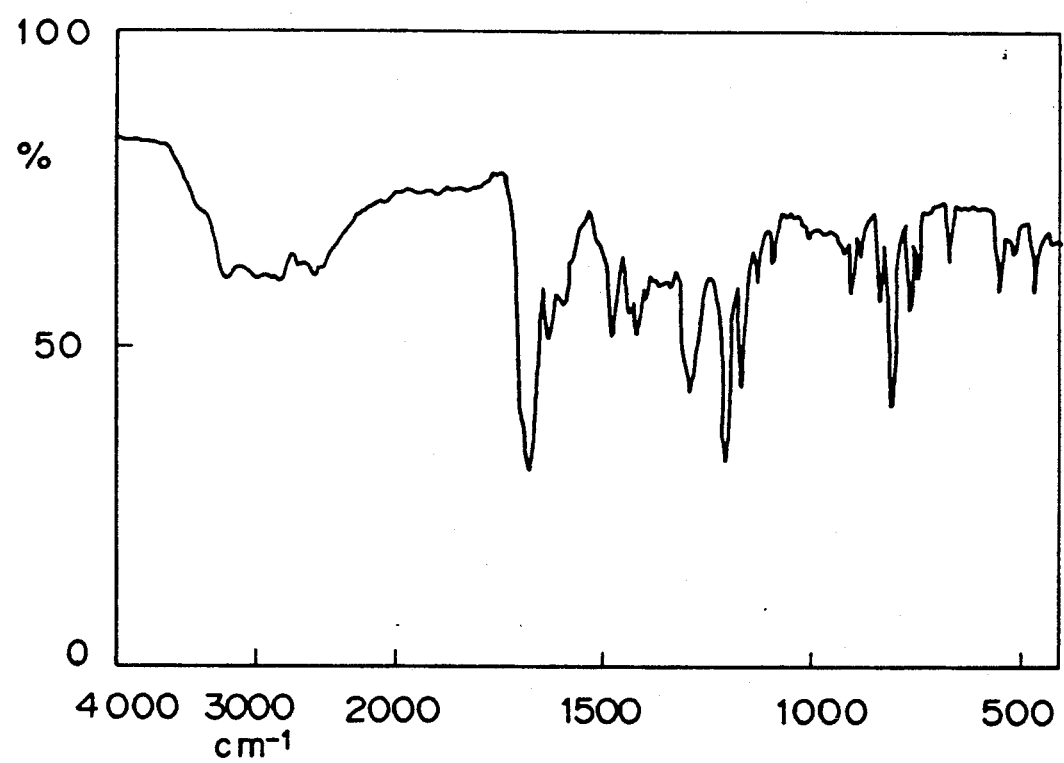
FIGS. 7–9 show the IR spectrum, NMR spectrum and mass spectrum of 2-(4'-hydroxyphenyl)-6-carboxylic acid, respectively.
Figure 8:
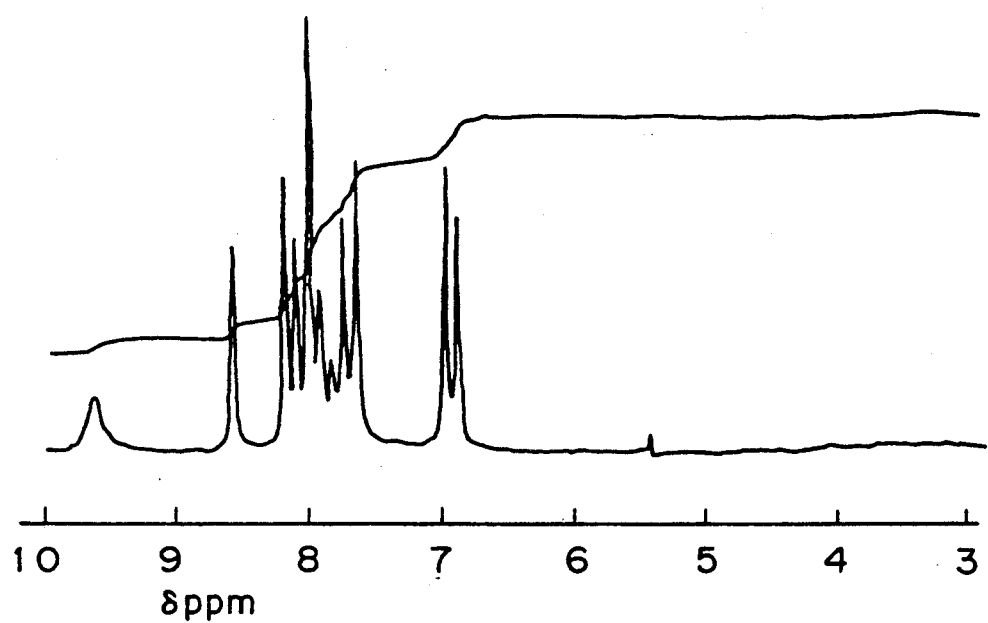
Figure 9:
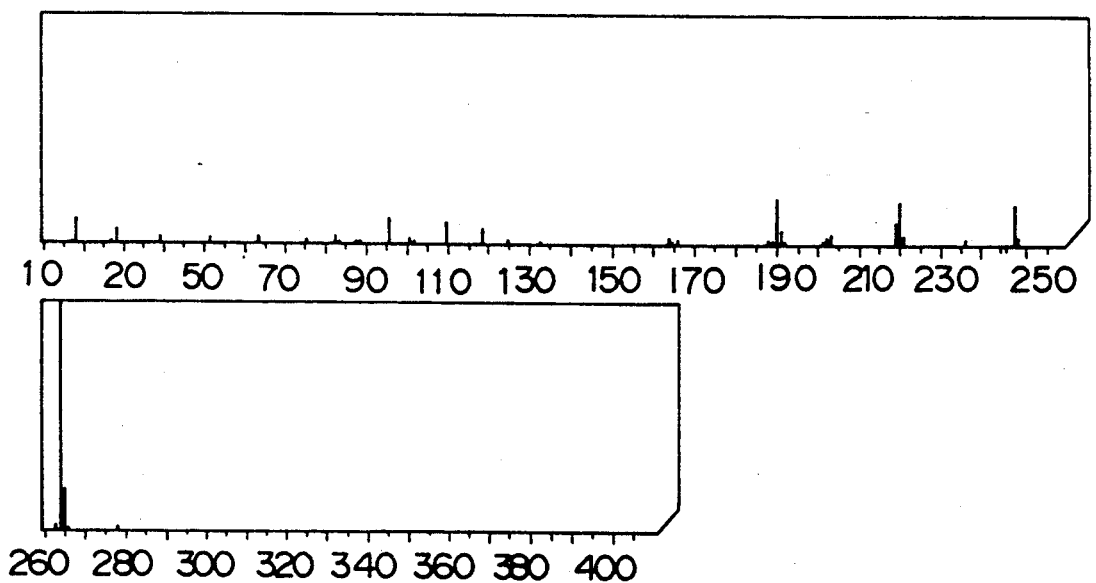

FIGS. 7-9 show that NMR spectrum, IR spectrum and MS spectrum of the resulting 2-(4'-hydroxyphenyl)-naphthalene-6-carboxylic acid, respectively. The polarizing microscope showed that the monomer obtained by reacting the above 2-(4'-hydroxyphenyl)naphthalene-6-carboxylic acid, n-nonanoic acid and 2-methyl butanol is in a smectic liquid crystallization at 54°-110° C.

2-(4'-hydroxyphenyl)naphthalene-6-carboxylic acid was obtained in a high yield according to the present invention.

The novel compound is useful as a hydroxy carboxylic acid for LCPs. Since a naphthalene group is attached to a phenyl group in the liquid crystal polymers derived from the above compound, the rigid properties of the polymer are relaxed and the melting point of the polymer is lowered. Therefore, the resulting liquid crystal polymers have excellent molding properties, thermal resistance and dielectric properties.

What is claimed is:
1. A compound represented by the formula:

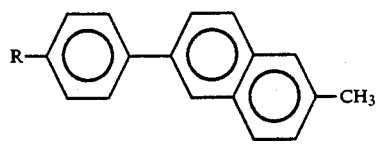

(2)

wherein R is $C_1$-$C_3$ alkyl or $C_1$-$C_3$ alkoxy.

2. A process for producing the compound of claim 1 which comprises:
   (a) acylating a compound selected from the group consisting of 4-alkoxy biphenyl and 4-alkyl biphenyl by subjecting said compound to Friedel-Crafts reaction with a 2-methyl butyryl halide and an aluminum halide to form a compound represented by the formula:

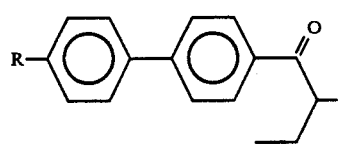

(3)

wherein R is as defined above;

(b) reducing the acylated compound of formula (3) with a suitable reducing agent to form a compound represented by the formula:

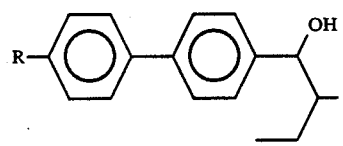

(4)

wherein R is as defined above;

(c) dehydrogenating the compound of formula (4) in the presence of an acid catalyst to form a compound represented by the formula:

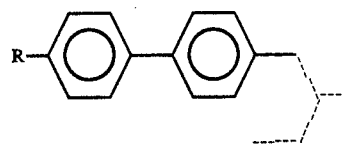

(5)

wherein R is as defined above and one of the four dotted lines is double bond and others are single bond; and (d) subjecting the compound of formula (5) to a vapor phase thermal reaction.

3. The process according to claim 2 wherein the acylating is effected at a temperature less than 10° C.

4. The process according to claim 3 wherein the reducing of said acylated compound is effected in the presence of a hydrogen sodium borate catalyst.

5. The process according to claim 2 wherein the reducing of said acylated compound is effected in the presence of copper chromate.

6. The process according to claim 2 wherein said acid catalyst is selected from the group consisting of para-toluene sulfonic acid, hydrochloric acid, dimethyl sulfoxide and gamma-alumina.

7. The process according to claim 2 wherein said vapor phase thermal reaction is effected in the presence of a catalyst selected from the group consisting of potassium alumina and potassium chromia.

8. A process for producing the compound according to claim 1 comprising:
(a) acylating a compound selected from the group consisting of 4-alkoxy biphenyl and 4-alkyl biphenyl by reacting said compound with carbon monoxide and 1-butene in the presence of HF-BF$_3$ catalyst to form a compound represented by the formula:

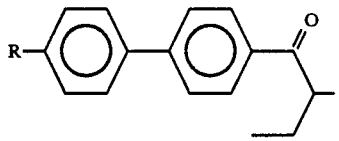
(3)

wherein R is as defined above;
(b) reducing said acylated compound with a suitable reducing agent to from a compound represented by the formula:

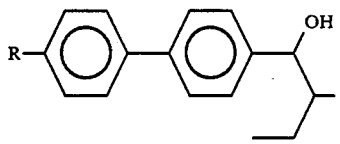
(4)

(c) dehydrogenating the compound of formula (4) in the presence of an acid catalyst to form a compound represented by the formula:

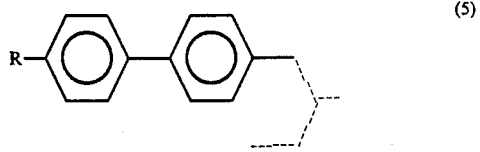
(5)

wherein R is as defined above and one of the four dotted lines is a double bond and the others are single bonds; and
(d) subjecting the compound of formula (5) to thermal vapor phase reaction in the presence of a catalyst containing a compound selected from the group consisting of alumina or chromia.

9. The process according to claim 8 wherein the reducing of said acylated compound is effected in the presence of a hydrogen sodium borate catalyst.

10. The process according to claim 8 wherein the reducing of said acylated compound is effected in the presence of copper chromate.

11. The process according to claim 8 wherein said acid catalyst is selected from the group consisting of para-toluene sulfonic acid, hydrochloric acid, dimethyl sulfoxide and gamma-alumina.

12. The process according to claim 8 wherein said vapor phase thermal reaction is effected in the presence of a catalyst selected from the group consisting of potassium alumina and potassium chromina.

* * * * *